US010292837B2

(12) United States Patent
Huff et al.

(10) Patent No.: US 10,292,837 B2
(45) Date of Patent: May 21, 2019

(54) DISASSEMBLY TOOL

(71) Applicant: DEPUY SYNTHES PRODUCTS, INC., Raynham, MA (US)

(72) Inventors: Daniel Huff, Warsaw, IN (US); Jeffrey A. McAnelly, Columbia City, IN (US); Lauren E. Penley, Cincinnati, OH (US); Rodney E. Satterthwaite, Huntington, IN (US)

(73) Assignee: DEPUY SYNTHES PRODUCTS INC., Raynham, MA (US)

( * ) Notice: Subject to any disclaimer, the term of this patent is extended or adjusted under 35 U.S.C. 154(b) by 0 days.

(21) Appl. No.: 15/848,660

(22) Filed: Dec. 20, 2017

(65) Prior Publication Data

US 2018/0110630 A1   Apr. 26, 2018

Related U.S. Application Data

(62) Division of application No. 14/745,633, filed on Jun. 22, 2015, now Pat. No. 9,867,720, which is a division
(Continued)

(51) Int. Cl.
*A61F 2/36* (2006.01)
*A61B 17/58* (2006.01)
(Continued)

(52) U.S. Cl.
CPC ............. *A61F 2/4637* (2013.01); *A61F 2/36* (2013.01); *A61F 2002/30579* (2013.01);
(Continued)

(58) Field of Classification Search
CPC .... A61F 2002/30579; A61F 2002/4641; A61F 2/36; A61F 2/4637
See application file for complete search history.

(56) References Cited

U.S. PATENT DOCUMENTS 422,013 A    2/1890  Ekstrom
650,795 A    5/1900  Maxwell
(Continued)

FOREIGN PATENT DOCUMENTS

DE    2823406 A1    12/1978
DE    3023942 A1    1/1982
(Continued)

OTHER PUBLICATIONS

Depuy Orthopaedics, Inc., "S-Rom Modular Hip System, Minimally Invasive Calcar Miller Surgical Technique," 0612-04-503, 2004, Depuy Orthopaedics, Inc.
(Continued)

*Primary Examiner* — Ann Schillinger

(57) ABSTRACT

A disassembly tool for disassembly of a first component of a prosthesis to a second component of the prosthesis for use in joint arthroplasty. The tool includes a first member having a radial portion operably associated with the first component and adapted to exert a radial force on the first component. A second member operably associated with the second component is also included and the second member has a second member longitudinal axis. A drive mechanism is coupled to the second member, such that as the drive mechanism is activated, the second member exerts a force against the second component in the direction of the longitudinal axis. Such exertion of force against the second member further causes the second member to move relative to the first member along the second member longitudinal axis.

6 Claims, 8 Drawing Sheets

Related U.S. Application Data of application No. 12/873,612, filed on Sep. 1, 2010, now Pat. No. 9,095,452.

(51) Int. Cl.
    *A61F 2/46* (2006.01)
    *A61F 2/30* (2006.01)

(52) U.S. Cl.
    CPC . *A61F 2002/4641* (2013.01); *Y10T 29/49815* (2015.01); *Y10T 29/53* (2015.01)

(56) References Cited

U.S. PATENT DOCUMENTS

| | | |
|---|---|---|
| 742,521 A | 10/1903 | Terry |
| 784,243 A | 3/1905 | Whalley |
| 1,029,402 A | 6/1912 | Ritter |
| 1,241,846 A | 10/1917 | Grons |
| 1,383,304 A | 7/1921 | Hughes |
| 1,423,649 A | 7/1922 | Daniel |
| 1,534,692 A | 4/1925 | Davis |
| 1,661,682 A | 3/1928 | Scherner |
| 2,234,824 A | 3/1941 | Kingston |
| 2,248,054 A | 7/1941 | Becker |
| 2,487,331 A | 11/1949 | Greene |
| 2,631,584 A | 3/1953 | Purificato |
| 2,661,033 A | 12/1953 | Daniel |
| 2,711,196 A | 6/1955 | Daniel |
| 2,834,099 A | 5/1958 | Gasper |
| 2,834,382 A | 5/1958 | Daniel |
| 2,856,637 A | 10/1958 | Daniel |
| 2,864,282 A | 12/1958 | Daniel |
| 2,877,936 A | 3/1959 | Michel |
| 2,895,154 A | 7/1959 | Belcher |
| 2,902,596 A | 9/1959 | Rockwell |
| 2,914,224 A | 11/1959 | Michel |
| 2,944,373 A | 7/1960 | Mentley |
| 2,955,905 A | 10/1960 | Davies |
| 2,957,610 A | 10/1960 | Michel |
| 2,974,699 A | 3/1961 | Boles |
| 2,975,944 A | 3/1961 | Michel |
| 2,977,726 A | 4/1961 | Daniel |
| 2,981,035 A | 4/1961 | Mentley |
| 2,994,461 A | 8/1961 | Michel |
| 2,994,988 A | 8/1961 | Mentley |
| 3,048,307 A | 8/1962 | Michel |
| 3,059,278 A | 10/1962 | Daniel |
| 3,071,862 A | 1/1963 | Daniel |
| 3,077,877 A | 2/1963 | Daniel |
| 3,092,934 A | 6/1963 | Daniel |
| 3,092,935 A | 6/1963 | Daniel |
| 3,101,875 A | 8/1963 | Michel |
| 3,135,136 A | 6/1964 | Mentley |
| 3,177,507 A | 4/1965 | Becker |
| 3,180,532 A | 4/1965 | Michel |
| 3,200,484 A | 8/1965 | Garman |
| 3,220,311 A | 11/1965 | Anthony |
| 3,250,745 A | 5/1966 | Davis |
| 3,293,987 A | 12/1966 | Daniel |
| 3,300,833 A | 1/1967 | Daniel |
| 3,301,134 A | 1/1967 | Daniel |
| 3,319,526 A | 5/1967 | Daniel |
| 3,331,115 A | 7/1967 | Daniel |
| 3,335,639 A | 8/1967 | Daniel |
| 3,424,783 A | 1/1969 | Harper |
| 3,443,478 A | 5/1969 | Daniel |
| 3,451,111 A | 6/1969 | Daniel |
| 3,479,387 A | 11/1969 | Daniels |
| 3,479,388 A | 11/1969 | Daniels |
| 3,483,175 A | 12/1969 | Harper |
| 3,494,752 A | 2/1970 | Daniel |
| 3,499,920 A | 3/1970 | Daniels |
| 3,541,868 A | 11/1970 | Hall |
| 3,580,027 A | 5/1971 | Daniel |
| 3,580,029 A | 5/1971 | Daniel |
| 3,604,235 A | 9/1971 | Motz |
| 3,629,981 A | 12/1971 | McCaffery |
| 3,631,703 A | 1/1972 | Bregi |
| 3,633,583 A | 1/1972 | Fishbein |
| 3,668,139 A | 6/1972 | Daniels |
| 3,673,887 A | 7/1972 | Daniel |
| 3,679,728 A | 7/1972 | Morgan |
| 3,679,729 A | 7/1972 | Daniels |
| 3,691,718 A | 9/1972 | Woodruff |
| 3,700,957 A | 10/1972 | Daniels |
| 3,705,513 A | 12/1972 | Daniel |
| 3,749,365 A | 7/1973 | Van Gompel |
| 3,754,586 A | 8/1973 | Daniels |
| 3,810,312 A | 5/1974 | Carson |
| 3,849,322 A | 11/1974 | Wendler |
| 3,862,483 A | 1/1975 | Kloster |
| 3,869,394 A | 3/1975 | Daniels |
| 3,889,558 A | 6/1975 | Duncan |
| 3,912,727 A | 10/1975 | Daniels |
| 3,987,499 A | 10/1976 | Scharbach |
| 4,004,581 A | 1/1977 | Heimke |
| 4,009,712 A | 3/1977 | Burstein |
| 4,035,988 A | 7/1977 | Daniels |
| 4,051,559 A | 10/1977 | Pifferi |
| D246,507 S | 11/1977 | Danielson |
| 4,115,875 A | 9/1978 | Rambert |
| 4,116,200 A | 9/1978 | Braun |
| 4,150,909 A | 4/1979 | Hibarger |
| D257,533 S | 11/1980 | Bevilacqua |
| D258,957 S | 4/1981 | Bevilacqua |
| 4,305,394 A | 12/1981 | Bertuch, Jr. |
| D266,768 S | 11/1982 | Bevilacqua |
| D267,151 S | 12/1982 | Bruce |
| 4,398,074 A | 8/1983 | Danielson |
| 4,420,864 A | 12/1983 | Hoyt |
| 4,457,306 A | 7/1984 | Borzone |
| 4,458,420 A | 7/1984 | Davis |
| D275,006 S | 8/1984 | Danielson |
| 4,473,070 A | 9/1984 | Matthews |
| 4,538,886 A | 9/1985 | Townsend |
| D282,246 S | 1/1986 | Thomas |
| D282,350 S | 1/1986 | Thomas |
| 4,601,289 A | 7/1986 | Chiarizzio |
| D285,073 S | 8/1986 | Danielson |
| D285,198 S | 8/1986 | Danielson |
| 4,608,055 A | 8/1986 | Morrey |
| D286,198 S | 10/1986 | Bancroft |
| D286,285 S | 10/1986 | Danielson |
| D287,494 S | 12/1986 | Danielson |
| D289,155 S | 4/1987 | Brooks |
| 4,658,808 A | 4/1987 | Link |
| D290,399 S | 6/1987 | Kitchens |
| 4,670,015 A | 6/1987 | Freeman |
| 4,686,971 A | 8/1987 | Harris |
| 4,686,978 A | 8/1987 | Wadsworth |
| 4,693,724 A | 9/1987 | Rhenter |
| 4,710,946 A | 12/1987 | Hinch |
| 4,716,894 A | 1/1988 | Lazzeri |
| 4,738,256 A | 4/1988 | Freeman |
| 4,777,942 A | 10/1988 | Frey |
| 4,830,147 A | 5/1989 | Kawada |
| D303,114 S | 8/1989 | Danielson |
| D304,587 S | 11/1989 | Danielson |
| 4,891,545 A | 1/1990 | Capek |
| 4,917,530 A | 4/1990 | Engelhardt |
| 4,923,422 A | 5/1990 | Capek |
| 4,938,773 A | 7/1990 | Strand |
| 4,959,066 A | 9/1990 | Dunn |
| 4,969,911 A | 11/1990 | Greene |
| D313,233 S | 12/1990 | Andrews, Sr. |
| D315,343 S | 3/1991 | Andrews |
| 4,997,621 A | 3/1991 | Johansson |
| 5,002,578 A | 3/1991 | Luman |
| 5,002,581 A | 3/1991 | Paxson |
| 5,015,255 A | 5/1991 | Kuslich |
| 5,016,858 A | 5/1991 | Mitchell |
| 5,020,519 A | 6/1991 | Hayes |
| D318,051 S | 7/1991 | Danielson |
| 5,033,180 A | 7/1991 | Colson |

(56) References Cited

U.S. PATENT DOCUMENTS

| | | |
|---|---|---|
| D319,439 S | 8/1991 | Danielson |
| 5,047,033 A | 9/1991 | Fallin |
| 5,049,150 A | 9/1991 | Cozad |
| D320,985 S | 10/1991 | Danielson |
| 5,053,037 A | 10/1991 | Lackey |
| 5,057,112 A | 10/1991 | Sherman |
| 5,060,505 A | 10/1991 | Tury |
| 5,061,271 A | 10/1991 | Van Zile |
| 5,080,685 A | 1/1992 | Bolesky |
| D323,657 S | 2/1992 | Danielson |
| 5,099,714 A | 3/1992 | Hutchison |
| 5,100,407 A | 3/1992 | Conrad |
| 5,108,452 A | 4/1992 | DeMane |
| 5,133,588 A | 7/1992 | Hutchinson |
| 5,135,529 A | 8/1992 | Paxson |
| 5,162,626 A | 11/1992 | Hutchison |
| 5,171,055 A | 12/1992 | Hutchison |
| 5,171,244 A | 12/1992 | Caspari |
| 5,181,928 A | 1/1993 | Bolesky |
| 5,184,017 A | 2/1993 | Tury |
| 5,190,548 A | 3/1993 | Davis |
| 5,190,550 A | 3/1993 | Miller |
| 5,192,283 A | 3/1993 | Ling |
| 5,197,989 A | 3/1993 | Hinckfuss |
| 5,201,882 A | 4/1993 | Paxson |
| 5,207,680 A | 5/1993 | Dietz |
| 5,218,814 A | 6/1993 | Teal |
| D337,639 S | 7/1993 | Beckman |
| 5,228,459 A | 7/1993 | Caspari |
| D338,473 S | 8/1993 | Patterson |
| 5,238,267 A | 8/1993 | Hutchison |
| 5,247,171 A | 9/1993 | Wlodarczyk |
| D340,461 S | 10/1993 | Patterson |
| 5,263,498 A | 11/1993 | Caspari |
| 5,290,313 A | 3/1994 | Heldreth |
| 5,304,181 A | 4/1994 | Caspari |
| D346,979 S | 5/1994 | Stalcup |
| 5,331,124 A | 7/1994 | Danielson |
| 5,336,226 A | 8/1994 | McDaniel |
| 5,342,363 A | 8/1994 | Richelsoph |
| 5,342,366 A | 8/1994 | Whiteside |
| 5,344,423 A | 9/1994 | Dietz |
| 5,345,483 A | 9/1994 | Johansson |
| 5,352,231 A | 10/1994 | Brumfield |
| D352,521 S | 11/1994 | Sculler |
| D353,394 S | 12/1994 | Stefanski |
| 5,370,706 A | 12/1994 | Bolesky |
| 5,372,209 A | 12/1994 | Raihert |
| D355,186 S | 2/1995 | Danielson |
| D355,187 S | 2/1995 | Danielson |
| 5,387,218 A | 2/1995 | Meswania |
| 5,395,376 A | 3/1995 | Caspari |
| D357,315 S | 4/1995 | Dietz |
| 5,403,320 A | 4/1995 | Luman |
| 5,405,404 A | 4/1995 | Gardner |
| 5,409,492 A | 4/1995 | Jones |
| 5,415,659 A | 5/1995 | Lee |
| 5,420,910 A | 5/1995 | Rudokas |
| D359,064 S | 6/1995 | Sculler |
| 5,422,478 A | 6/1995 | Wlodarczyk |
| 5,457,100 A | 10/1995 | Daniel |
| 5,459,294 A | 10/1995 | Danielson |
| D364,621 S | 11/1995 | Clarke |
| 5,468,243 A | 11/1995 | Halpern |
| 5,470,336 A | 11/1995 | Ling |
| 5,474,559 A | 12/1995 | Bertin |
| 5,476,466 A | 12/1995 | Barrette |
| D365,824 S | 1/1996 | Danielson |
| 5,486,180 A | 1/1996 | Dietz |
| 5,496,324 A | 3/1996 | Barnes |
| 5,507,815 A | 4/1996 | Wagner |
| 5,507,824 A | 4/1996 | Lennox |
| 5,507,830 A | 4/1996 | DeMane |
| 5,507,833 A | 4/1996 | Bohn |
| 5,519,929 A | 5/1996 | Bleckman |
| 5,527,316 A | 6/1996 | Stone |
| 5,528,640 A | 6/1996 | Johansson |
| 5,534,005 A | 7/1996 | Tokish, Jr. |
| 5,540,687 A | 7/1996 | Fairley |
| 5,540,694 A | 7/1996 | DeCarlo, Jr. |
| 5,555,551 A | 9/1996 | Rudokas |
| 5,569,255 A | 10/1996 | Burke |
| D376,527 S | 12/1996 | Apolinski |
| 5,591,233 A | 1/1997 | Kelman |
| 5,593,411 A | 1/1997 | Stalcup |
| 5,593,452 A | 1/1997 | Higham |
| 5,600,892 A | 2/1997 | Peugh |
| 5,601,563 A | 2/1997 | Burke |
| 5,601,567 A | 2/1997 | Swajger |
| 5,607,269 A | 3/1997 | Dowd |
| 5,607,431 A | 3/1997 | Dudasik |
| D379,578 S | 6/1997 | Daniels |
| 5,643,271 A | 7/1997 | Sederholm |
| 5,645,607 A | 7/1997 | Hickey |
| 5,653,714 A | 8/1997 | Dietz |
| 5,653,764 A | 8/1997 | Murphy |
| 5,653,765 A | 8/1997 | McTighe |
| 5,658,349 A | 8/1997 | Brooks |
| 5,663,993 A | 9/1997 | Danielson |
| 5,669,812 A | 9/1997 | Schockemoehl |
| 5,683,395 A | 11/1997 | Mikhail |
| D387,962 S | 12/1997 | Apolinski |
| D387,963 S | 12/1997 | Clark |
| 5,697,932 A | 12/1997 | Smith |
| 5,702,480 A | 12/1997 | Kropf |
| 5,702,487 A | 12/1997 | Averill |
| 5,420,910 B1 | 2/1998 | Rudokas |
| 5,715,672 A | 2/1998 | Schockemoehl |
| D392,534 S | 3/1998 | Degen |
| D392,866 S | 3/1998 | Degen |
| 5,725,592 A | 3/1998 | White |
| 5,728,128 A | 3/1998 | Crickenberger |
| 5,735,857 A | 4/1998 | Lane |
| 5,743,915 A | 4/1998 | Bertin |
| 5,752,972 A | 5/1998 | Hoogeboom |
| 5,755,803 A | 5/1998 | Haines |
| 5,766,261 A | 6/1998 | Neal |
| 5,769,855 A | 6/1998 | Bertin |
| 5,776,200 A | 7/1998 | Johnson |
| 5,782,921 A | 7/1998 | Colleran |
| 5,792,143 A | 8/1998 | Samuelson |
| 5,800,553 A | 9/1998 | Albrektsson |
| 5,804,886 A | 9/1998 | Danielson |
| 5,810,827 A | 9/1998 | Haines |
| 5,810,829 A | 9/1998 | Elliott |
| 5,810,830 A | 9/1998 | Noble |
| 5,824,097 A | 10/1998 | Gabriel |
| 5,849,015 A | 12/1998 | Haywood |
| 5,850,162 A | 12/1998 | Danielsons |
| 5,853,415 A | 12/1998 | Bertin |
| 5,858,020 A | 1/1999 | Johnson |
| 5,858,828 A | 1/1999 | Seliskar |
| 5,860,969 A | 1/1999 | White |
| 5,860,981 A | 1/1999 | Bertin |
| 5,876,459 A | 3/1999 | Powell |
| 5,879,354 A | 3/1999 | Haines |
| 5,879,391 A | 3/1999 | Slamin |
| 5,890,966 A | 4/1999 | Costain |
| 5,902,340 A | 5/1999 | White |
| 5,906,644 A | 5/1999 | Powell |
| 5,908,423 A | 6/1999 | Kashuba |
| 5,919,195 A | 7/1999 | Wilson |
| 5,923,422 A | 7/1999 | Keens |
| 5,935,172 A | 8/1999 | Ochoa |
| 5,938,701 A | 8/1999 | Hiernard |
| 5,950,121 A | 9/1999 | Kaminsky |
| 5,951,606 A | 9/1999 | Burke |
| 5,954,460 A | 9/1999 | Degen |
| 5,957,768 A | 9/1999 | Schockemoehl |
| 5,957,925 A | 9/1999 | Cook |
| 5,966,599 A | 10/1999 | Walker |
| 5,968,049 A | 10/1999 | Da Rold |
| 5,973,064 A | 10/1999 | Zhao |
| 5,976,145 A | 11/1999 | Kennefick, III |

(56) References Cited

U.S. PATENT DOCUMENTS

| | | |
|---|---|---|
| 5,976,147 A | 11/1999 | LaSalle |
| 5,976,188 A | 11/1999 | Dextradeur |
| 5,993,455 A | 11/1999 | Noble |
| 5,996,812 A | 12/1999 | Sokol, Jr. |
| 5,997,419 A | 12/1999 | Daniels |
| 6,013,082 A | 1/2000 | Hiernard |
| 6,045,556 A | 4/2000 | Cohen |
| 6,048,365 A | 4/2000 | Burrows |
| 6,054,895 A | 4/2000 | Danielsons |
| 6,056,084 A | 5/2000 | Schockemoehl |
| 6,056,754 A | 5/2000 | Haines |
| 6,058,301 A | 5/2000 | Daniels |
| 6,059,528 A | 5/2000 | Danielson |
| 6,063,123 A | 5/2000 | Burrows |
| 6,069,048 A | 5/2000 | Daniel |
| 6,071,311 A | 6/2000 | O'Neil |
| 6,077,783 A | 6/2000 | Allman |
| 6,080,162 A | 6/2000 | Dye |
| 6,090,146 A | 7/2000 | Rozow, III |
| 6,096,625 A | 8/2000 | Daniel |
| 6,110,179 A | 8/2000 | Flivik |
| 6,117,138 A | 9/2000 | Burrows |
| 6,120,507 A | 9/2000 | Allard |
| 6,121,147 A | 9/2000 | Daniel |
| 6,126,694 A | 10/2000 | Gray, Jr. |
| 6,136,035 A | 10/2000 | Lob |
| 6,139,581 A | 10/2000 | Engh |
| 6,149,687 A | 11/2000 | Gray, Jr. |
| 6,159,214 A | 12/2000 | Michelson |
| 6,162,226 A | 12/2000 | DeCarlo, Jr. |
| 6,165,177 A | 12/2000 | Wilson |
| 6,179,116 B1 | 1/2001 | Noniewicz |
| 6,179,877 B1 | 1/2001 | Burke |
| 6,181,925 B1 | 1/2001 | Kaminsky |
| 6,185,416 B1 | 2/2001 | Rudokas |
| 6,187,012 B1 | 2/2001 | Masini |
| 6,193,759 B1 | 2/2001 | Ro |
| 6,197,064 B1 | 3/2001 | Haines |
| 6,197,065 B1 | 3/2001 | Martin |
| 6,201,253 B1 | 3/2001 | Allman |
| 6,206,884 B1 | 3/2001 | Masini |
| 6,219,538 B1 | 4/2001 | Kaminsky |
| 6,224,605 B1 | 5/2001 | Anderson |
| 6,232,721 B1 | 5/2001 | Danielsons |
| 6,235,590 B1 | 5/2001 | Daniel |
| 6,238,435 B1 | 5/2001 | Meulink |
| 6,238,436 B1 | 5/2001 | Lob |
| D443,882 S | 6/2001 | Daniels |
| 6,241,847 B1 | 6/2001 | Allman |
| 6,242,978 B1 | 6/2001 | Danielsons |
| 6,258,093 B1 | 7/2001 | Edwards |
| 6,258,095 B1 | 7/2001 | Lombardo |
| 6,258,097 B1 | 7/2001 | Cook |
| 6,260,279 B1 | 7/2001 | Apolinski |
| 6,263,998 B1 | 7/2001 | Schockemoehl |
| 6,264,699 B1 | 7/2001 | Noiles |
| 6,270,502 B1 | 8/2001 | Stulberg |
| 6,281,935 B1 | 8/2001 | Twitchell |
| 6,285,871 B1 | 9/2001 | Daniels |
| 6,287,342 B1 | 9/2001 | Copf |
| 6,310,410 B1 | 10/2001 | Lin |
| D450,304 S | 11/2001 | Daniels |
| 6,316,817 B1 | 11/2001 | Seliskar |
| 6,318,651 B1 | 11/2001 | Spiering |
| 6,319,286 B1 | 11/2001 | Fernandez |
| 6,330,845 B1 | 12/2001 | Meulink |
| 6,332,886 B1 | 12/2001 | Green |
| 6,335,766 B1 | 1/2002 | Twitchell |
| 6,354,908 B2 | 3/2002 | Allman |
| 6,355,068 B1 | 3/2002 | Doubler |
| 6,355,532 B1 | 3/2002 | Seliskar |
| 6,361,563 B2 | 3/2002 | Terrill Grisoni |
| 6,366,422 B1 | 4/2002 | Daniel |
| 6,372,520 B1 | 4/2002 | Hsia |
| D457,176 S | 5/2002 | Daniels |
| 6,382,276 B1 | 5/2002 | Daniels |
| D458,947 S | 6/2002 | Svetlik |
| 6,400,415 B1 | 6/2002 | Danielsons |
| 6,406,217 B1 | 6/2002 | Daniel |
| 6,419,147 B1 | 7/2002 | Daniel |
| 6,422,562 B1 | 7/2002 | Daniel |
| 6,422,816 B1 | 7/2002 | Danielson |
| 6,428,578 B2 | 8/2002 | White |
| 6,432,110 B1 | 8/2002 | Richelsoph |
| 6,432,141 B1 | 8/2002 | Stocks |
| 6,440,139 B2 | 8/2002 | Michelson |
| D467,485 S | 12/2002 | Daniels |
| 6,488,713 B1 | 12/2002 | Hershberger |
| 6,491,696 B1 | 12/2002 | Kunkel |
| D468,180 S | 1/2003 | Bruno |
| 6,505,684 B2 | 1/2003 | Rayssiguier |
| 6,508,841 B2 | 1/2003 | Martin |
| D469,671 S | 2/2003 | Prell |
| 6,517,581 B2 | 2/2003 | Blamey |
| RE38,058 E | 4/2003 | Fallin |
| 6,565,029 B2 | 5/2003 | Zweighaft |
| 6,568,618 B1 | 5/2003 | Vanderheyden |
| 6,589,284 B1 | 7/2003 | Silberer |
| 6,589,285 B2 | 7/2003 | Penenberg |
| 6,600,516 B1 | 7/2003 | Danielsons |
| 6,609,900 B2 | 8/2003 | Lucke |
| 6,613,091 B1 | 9/2003 | Zdeblick |
| 6,663,616 B1 | 12/2003 | Roth |
| 6,676,706 B1 | 1/2004 | Mears |
| 6,679,917 B2 | 1/2004 | Ek |
| 6,682,568 B2 | 1/2004 | Despres, III |
| 6,692,530 B2 | 2/2004 | Doubler |
| 6,700,359 B2 | 3/2004 | Daniels |
| 6,702,854 B1 | 3/2004 | Cheal |
| 6,706,072 B2 | 3/2004 | Dwyer |
| 6,706,621 B2 | 3/2004 | Cox |
| 6,712,825 B2 | 3/2004 | Aebi |
| 6,723,129 B2 | 4/2004 | Dwyer |
| 6,740,090 B1 | 5/2004 | Cragg |
| 6,743,235 B2 | 6/2004 | Subba Rao |
| 6,744,243 B2 | 6/2004 | Daniels |
| 6,751,266 B1 | 6/2004 | Danielsons |
| 6,755,841 B2 | 6/2004 | Fraser |
| 6,770,100 B2 | 8/2004 | Draenert |
| 6,793,208 B1 | 9/2004 | Riddle, Jr. |
| D497,499 S | 10/2004 | Daniel |
| 6,811,376 B2 | 11/2004 | Arel |
| 6,812,792 B2 | 11/2004 | Mattsson |
| 6,824,552 B2 | 11/2004 | Robison |
| 6,840,944 B2 | 1/2005 | Suddaby |
| 6,846,314 B2 | 1/2005 | Shapira |
| 6,856,029 B1 | 2/2005 | Daniel |
| 6,870,160 B1 | 3/2005 | Daniel |
| 6,875,218 B2 | 4/2005 | Dye |
| 6,883,217 B2 | 4/2005 | Barrette |
| D505,611 S | 5/2005 | Daniel |
| 6,905,515 B1 | 6/2005 | Gilbertson |
| 6,911,048 B2 | 6/2005 | Fernandez |
| 6,949,101 B2 | 9/2005 | McCleary |
| 6,990,691 B2 | 1/2006 | Klotz |
| 6,997,930 B1 | 2/2006 | Jäggi |
| 7,001,392 B2 | 2/2006 | McGovern |
| 7,008,420 B2 | 3/2006 | Okada |
| 7,022,141 B2 | 4/2006 | Dwyer |
| 7,066,042 B2 | 6/2006 | Andrews |
| 7,074,224 B2 | 7/2006 | Daniels |
| 7,188,556 B1 | 3/2007 | Rinner |
| 7,189,242 B2 | 3/2007 | Boyd |
| 7,204,851 B2 | 4/2007 | Trieu |
| 7,297,166 B2 * | 11/2007 | Dwyer .................. A61F 2/36 606/99 |
| 7,363,838 B2 | 4/2008 | Abdelgany |
| 7,373,709 B2 | 5/2008 | Fernando |
| 7,387,635 B2 | 6/2008 | Keller |
| 7,425,214 B1 | 9/2008 | McCarthy |
| 7,431,723 B2 | 10/2008 | Hazebrouck |
| 7,582,092 B2 | 9/2009 | Jones |
| 7,585,329 B2 | 9/2009 | McCleary |
| 7,601,155 B2 | 10/2009 | Petersen |

(56) References Cited

U.S. PATENT DOCUMENTS

| | | |
|---|---|---|
| 7,641,658 B2 | 1/2010 | Shaolian |
| 8,696,758 B2 | 4/2014 | Hood |
| 8,702,807 B2 | 4/2014 | Hood |
| 8,900,246 B2 | 12/2014 | Lashure |
| 8,998,919 B2 | 4/2015 | Jones |
| 2001/0001121 A1 | 5/2001 | Lombardo |
| 2001/0007957 A1 | 7/2001 | Martin |
| 2001/0016779 A1 | 8/2001 | Lubinus |
| 2001/0021621 A1 | 9/2001 | Moore |
| 2001/0021622 A1 | 9/2001 | Allman |
| 2001/0034526 A1 | 10/2001 | Kuslich |
| 2002/0004684 A1 | 1/2002 | Thomas |
| 2002/0038148 A1 | 3/2002 | Fernandez |
| 2002/0043296 A1 | 4/2002 | Daniels |
| 2002/0058999 A1 | 5/2002 | Dwyer |
| 2002/0059000 A1 | 5/2002 | Dwyer |
| 2002/0127115 A1 | 9/2002 | Lucke |
| 2002/0133233 A1 | 9/2002 | Blamey |
| 2002/0183758 A1 | 12/2002 | Middleton |
| 2002/0195512 A1 | 12/2002 | Zweighft |
| 2003/0001551 A1 | 1/2003 | Daniels |
| 2003/0048003 A1 | 3/2003 | Daniels |
| 2003/0050645 A1 | 3/2003 | Parker |
| 2003/0071329 A1 | 4/2003 | Cox |
| 2003/0074080 A1 | 4/2003 | Murray |
| 2003/0093080 A1 | 5/2003 | Brown |
| 2003/0095368 A1 | 5/2003 | Daniels |
| 2003/0109882 A1 | 6/2003 | Shirado |
| 2003/0114933 A1 | 6/2003 | Bouttens |
| 2003/0130740 A1 | 7/2003 | Stocks |
| 2003/0149487 A1 | 8/2003 | Doubler |
| 2003/0171756 A1 | 9/2003 | Fallin |
| 2003/0171816 A1 | 9/2003 | Scifert |
| 2003/0180146 A1 | 9/2003 | Arel |
| 2003/0187449 A1 | 10/2003 | McCleary |
| 2003/0204269 A1 | 10/2003 | Gerbec |
| 2003/0220698 A1 | 11/2003 | Mears |
| 2003/0225417 A1 | 12/2003 | Fischell |
| 2003/0228033 A1 | 12/2003 | Daniel |
| 2004/0010262 A1 | 1/2004 | Parkinson |
| 2004/0010319 A1 | 1/2004 | McTighe |
| 2004/0015239 A1 | 1/2004 | Beguec |
| 2004/0017085 A1 | 1/2004 | Daniels |
| 2004/0054373 A1 | 3/2004 | Serra |
| 2004/0054419 A1 | 3/2004 | Serra |
| 2004/0058997 A1 | 3/2004 | Daniel |
| 2004/0064186 A1 | 4/2004 | McCleary |
| 2004/0066217 A1 | 4/2004 | Daniels |
| 2004/0073315 A1 | 4/2004 | Justin |
| 2004/0092951 A1 | 5/2004 | Serra |
| 2004/0111861 A1 | 6/2004 | Barrette |
| 2004/0122437 A1 | 6/2004 | Dwyer |
| 2004/0122439 A1 | 6/2004 | Dwyer |
| 2004/0122440 A1 | 6/2004 | Daniels |
| 2004/0122525 A1 | 6/2004 | Daniels |
| 2004/0130394 A1 | 7/2004 | Mattsson |
| 2004/0135233 A1 | 7/2004 | Cox |
| 2004/0147933 A1 | 7/2004 | McGovern |
| 2004/0167527 A1 | 8/2004 | Simon |
| 2004/0172138 A1 | 9/2004 | May |
| 2004/0172139 A1 | 9/2004 | Dwyer |
| 2004/0210471 A1 | 10/2004 | Luby |
| 2004/0211046 A1 | 10/2004 | Tally |
| 2004/0236342 A1 | 11/2004 | Ferree |
| 2004/0260297 A1 | 12/2004 | Padget |
| 2004/0267266 A1 | 12/2004 | Daniels |
| 2004/0267267 A1 | 12/2004 | Daniels |
| 2004/0267372 A1 | 12/2004 | Vanasse |
| 2004/0267373 A1 | 12/2004 | Dwyer |
| 2005/0004679 A1 | 1/2005 | Sederholm |
| 2005/0010992 A1 | 1/2005 | Klotz |
| 2005/0015049 A1 | 1/2005 | Rioux |
| 2005/0033444 A1 | 2/2005 | Jones |
| 2005/0047239 A1 | 3/2005 | Takahashi |
| 2005/0078289 A1 | 4/2005 | Daniel |
| 2005/0081910 A1 | 4/2005 | Danielson |
| 2005/0085820 A1 | 4/2005 | Collins |
| 2005/0115391 A1 | 6/2005 | Baker |
| 2005/0154331 A1 | 7/2005 | Christie |
| 2005/0188878 A1 | 9/2005 | Baker |
| 2005/0209597 A1 | 9/2005 | Long |
| 2005/0222572 A1 | 10/2005 | Chana |
| 2005/0234461 A1 | 10/2005 | Burdulis |
| 2005/0234462 A1 | 10/2005 | Hershberger |
| 2005/0234559 A1 | 10/2005 | Fernandez |
| 2005/0240193 A1 | 10/2005 | Layne |
| 2005/0261702 A1 | 11/2005 | Oribe |
| 2005/0267937 A1 | 12/2005 | Daniels |
| 2005/0288676 A1 | 12/2005 | Schnieders |
| 2006/0015110 A1 | 1/2006 | Pepper |
| 2006/0015112 A1 | 1/2006 | McGovern |
| 2006/0024656 A1 | 2/2006 | Morris |
| 2006/0027027 A1 | 2/2006 | Serra |
| 2006/0058810 A1 | 3/2006 | Wozencroft |
| 2006/0106393 A1 | 5/2006 | Huebner |
| 2006/0217737 A1 | 9/2006 | Iversen |
| 2006/0260440 A1 | 11/2006 | Abdelgany |
| 2007/0005144 A1 | 1/2007 | Leisinger |
| 2007/0100464 A1 | 5/2007 | Meulink |
| 2007/0123908 A1 | 5/2007 | Jones |
| 2007/0162033 A1 | 7/2007 | Daniels |
| 2007/0179502 A1 | 8/2007 | Raynor |
| 2007/0233132 A1 | 10/2007 | Valla |
| 2007/0244566 A1 | 10/2007 | Daniels |
| 2007/0260315 A1 | 11/2007 | Foley |
| 2007/0299534 A1 | 12/2007 | Lewis |
| 2008/0065081 A1 | 3/2008 | Lechot |
| 2008/0077156 A1 | 3/2008 | Emstad |
| 2008/0091212 A1 | 4/2008 | Dwyer |
| 2008/0114367 A1 | 5/2008 | Meyer |
| 2008/0133024 A1 | 6/2008 | Meswania |
| 2008/0161811 A1 | 7/2008 | Daniels |
| 2008/0188878 A1 | 8/2008 | Young |
| 2008/0275457 A1 | 11/2008 | Meek |
| 2009/0112216 A1 | 4/2009 | Leisinger |
| 2009/0112218 A1 | 4/2009 | McCleary |
| 2009/0187251 A1 | 7/2009 | Justin |
| 2009/0228012 A1 | 9/2009 | Gangji |
| 2009/0307887 A1 | 12/2009 | Jones |
| 2010/0069909 A1 | 3/2010 | Taylor |
| 2010/0107829 A1 | 5/2010 | Zimmerman |
| 2010/0145345 A1 | 6/2010 | Ammann |
| 2010/0168752 A1 | 7/2010 | Edwards |
| 2010/0249943 A1 | 9/2010 | Bergin |
| 2011/0054628 A1 | 3/2011 | Banks |
| 2011/0071527 A1 | 3/2011 | Nelson |
| 2011/0302760 A1 | 12/2011 | Leisinger |
| 2012/0053698 A1 | 3/2012 | Huff |
| 2012/0259341 A1 | 10/2012 | McCleary |
| 2012/0259421 A1 | 10/2012 | Satterthwaite |

FOREIGN PATENT DOCUMENTS

| | | |
|---|---|---|
| DE | 3538654 A1 | 4/1987 |
| DE | 10014401 A1 | 6/2001 |
| DE | 20114835 U1 | 1/2002 |
| DE | 202006000845 U1 | 5/2006 |
| DE | 202012102017 U1 | 10/2013 |
| EP | 206777 A2 | 12/1986 |
| EP | 239711 A1 | 10/1987 |
| EP | 333990 A2 | 9/1989 |
| EP | 511244 A1 | 11/1992 |
| EP | 595956 A1 | 5/1994 |
| EP | 661023 A2 | 7/1995 |
| EP | 726063 A1 | 8/1996 |
| EP | 728449 A2 | 8/1996 |
| EP | 842639 A2 | 5/1998 |
| EP | 861635 A2 | 9/1998 |
| EP | 1000595 A1 | 5/2000 |
| EP | 1013245 A2 | 6/2000 |
| EP | 1080701 A2 | 3/2001 |
| EP | 1084680 A2 | 3/2001 |
| EP | 1191906 A1 | 4/2002 |
| EP | 1201191 A1 | 5/2002 |

(56) References Cited

FOREIGN PATENT DOCUMENTS

| | | |
|---|---|---|
| EP | 1263334 A2 | 12/2002 |
| EP | 1323395 A2 | 7/2003 |
| EP | 1348384 A2 | 10/2003 |
| EP | 1369089 A2 | 12/2003 |
| EP | 1435223 A1 | 7/2004 |
| EP | 1493407 A2 | 1/2005 |
| EP | 1522284 A2 | 4/2005 |
| EP | 1591084 A1 | 11/2005 |
| EP | 1080701 B1 | 8/2006 |
| EP | 1738723 A1 | 1/2007 |
| EP | 1905396 A1 | 4/2008 |
| EP | 2055273 A1 | 5/2009 |
| EP | 2057969 A2 | 5/2009 |
| FR | 2606628 A1 | 5/1988 |
| FR | 2699400 A1 | 6/1994 |
| FR | 2737107 A1 | 1/1997 |
| FR | 2828397 A1 | 2/2003 |
| FR | 2832624 A1 | 5/2003 |
| FR | 2926208 A1 | 7/2009 |
| FR | 2926212 A1 | 7/2009 |
| GB | 250441 A | 6/1992 |
| JP | 5148516 A | 6/1993 |
| JP | 5212069 A | 8/1993 |
| JP | 6500039 A | 1/1994 |
| JP | 10080095 A | 3/1998 |
| JP | 2000210314 A | 8/2000 |
| JP | 2002153479 A | 5/2002 |
| JP | 2002238912 A | 8/2002 |
| JP | 2003339724 A | 12/2003 |
| JP | 2004223261 A | 8/2004 |
| JP | 2004251450 A | 9/2004 |
| JP | 2006501917 T | 1/2006 |
| JP | 2006523106 A | 10/2006 |
| JP | 2007061154 A | 3/2007 |
| JP | 2007503911 A | 3/2007 |
| JP | 2007508063 A | 4/2007 |
| JP | 2010540179 A | 12/2010 |
| JP | 5212069 B2 | 6/2013 |
| WO | WO 1991010408 A1 | 7/1991 |
| WO | WO 1992010138 A1 | 6/1992 |
| WO | WO 1993001769 A1 | 2/1993 |
| WO | WO 1994012123 A1 | 6/1994 |
| WO | WO 1994027507 A1 | 12/1994 |
| WO | WO 1996015738 A1 | 5/1996 |
| WO | WO 1996015739 A1 | 5/1996 |
| WO | WO 1999020196 A1 | 4/1999 |
| WO | WO 2001067997 A1 | 9/2001 |
| WO | WO 2002102254 A2 | 12/2002 |
| WO | WO 2003015642 A1 | 2/2003 |
| WO | WO 2003065906 A2 | 8/2003 |
| WO | WO 2003082159 A1 | 10/2003 |
| WO | WO 2003092513 A1 | 11/2003 |
| WO | WO 2003094698 A2 | 11/2003 |
| WO | WO 2003094803 A1 | 11/2003 |
| WO | WO 2004028266 A1 | 4/2004 |
| WO | WO 2004032767 A1 | 4/2004 |
| WO | WO 2004089224 A2 | 10/2004 |
| WO | WO 2005034817 A1 | 4/2005 |
| WO | WO 2007026119 A1 | 3/2007 |
| WO | WO 2007098549 A1 | 9/2007 |
| WO | WO 2007106752 A2 | 9/2007 |
| WO | WO 2008069800 A1 | 6/2008 |
| WO | WO 2009024798 A1 | 2/2009 |
| WO | WO 2012138824 A2 | 10/2012 |

OTHER PUBLICATIONS

Engage Modular Revision Hip System: Surgical Technique, 2007, DePuy Orthopaedics, Inc, 19 pages.

Gray, John R.; Clinically-Oriented Geometry of the Femur; A thesis submitted to the School of Physical & Health Education in partial fulfillment of requirements for the degree of Master of Science, Queen's University, Kingston, Ontario, Canada, Aug. 1995, 73 pages.

Paul, H.A., et al. "Development of a Surgical Robot for Cementless Total Hip Arthroplasty," Clinical Orthopedics & Related Research 285 Dec. 1992: 57-66.

S-Rom Modular Hip System, retrieved from Johnson & Johnson Gateway web site http://www.jnj.gateway.com/home.jhtml?loc=USENG&page-viewContent&contented=fc0de0010000030, retrieved on Sep. 26, 2005, 1 page.

Zimmer Fracture Equipment & Orthopaedic Appliances, 1 page, published at least as early as Sep. 29, 2005.

Zimmer Metasul LDH Large Diameter Head; Surgical Technique Enhancing Stability and Increasing Range of Motion, available at least as early as Sep. 28, 2006 (19 pages).

\* cited by examiner

DISASSEMBLY TOOL

CROSS REFERENCE TO RELATED APPLICATION

The present application is a divisional of U.S. application Ser. No. 14/745,633, filed Jun. 22, 2015, which is a divisional of U.S. application Ser. No. 12/873,612, filed Sep. 1, 2010, now issued U.S. Pat. No. 9,095,452, granted Aug. 4, 2015, both of which are incorporated by reference in their entireties.

TECHNICAL FIELD

The present invention relates generally to the field of orthopaedics, and more particularly, to an implant for use in arthroplasty.

BACKGROUND

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

Many designs and methods for manufacturing implantable articles, such as bone prostheses, are known. Such bone prostheses include components of artificial joints such as elbows, hips, knees and shoulders.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. Such variations may be due to, for example, the patient's age, size and gender. For example, in the case of a femoral prosthesis, the patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femoral canal.

Such a need for prostheses of varying shapes and sizes thus creates a number of problems in regard to the use of a one-piece prosthesis. For example, a hospital or surgery center must maintain a relatively large inventory of prostheses in order to have the requisite mix of prostheses needed for certain situations, such as trauma situations and revision surgery. Moreover, since the bow of the stem must conform to the bow of the intramedullary canal of the patient's femur rotational positioning of the upper portion of the prosthesis is limited thereby rendering precise location of the upper portion and hence the head of the prosthesis very difficult. In addition, since corresponding bones of the left and right side of a patient's anatomy (e.g. left and right femur) may bow in opposite directions, it is necessary to provide (left) and (right) variations of the prosthesis in order to provide anteversion of the bone stem, thereby further increasing the inventory of prostheses which must be maintained.

As a result of these and other drawbacks, a number of modular prostheses have been designed. As its name implies, a modular prosthesis is constructed in modular form so that the individual elements or figures of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position that conforms to the patient's anatomy while also allowing for a limited degree of independent positioning of the proximal neck component relative to the patient's pelvis.

One issue that arises as a result of the use of a modular prosthesis is the locking of the components relative to one another. In particular, firm, reproducible, locking of the proximal neck component to the distal stem component is critical to prevent separation of the two components subsequent to implantation thereof into the patient. The need for the firm locking is particularly necessary if the design does not provide for positive locking with weight bearing. As such, a number of locking mechanisms have heretofore been designed to lock the components of a modular prosthesis to one another. For example, a number of modular prostheses have heretofore been designed to include a distal stem component which has an upwardly extending post which is received into a bore defined distal neck component. A relatively long fastener such as a screw or bolt is utilized to secure the post with the bore. Other methods of securing modular components include the impacting of one component onto the other. This method has highly variable results.

Current designs of modular stems include designs in which the modular connection utilizes a tapered fit between the two components. For example, the proximal body may include an internal taper which mates with an external taper on the distal stem. Such a taper connection may be used in conjunction with additional securing means, for example, a threaded connection or may be used alone. It is important that the tapered connection be secure. For example, the proper amount of force must be applied to the tapered connection to properly secure the tapered connection so that the connection can withstand the forces associated with the operation of the stem.

Because the modular pieces need to be securely joined, it is sometimes difficult to separate them if the need arises. For example, in some cases, during the hip replacement surgery, the surgeon may determine (after assembling the modular pieces) that a different proximal body needs to be used. In such a case, the original proximal body needs to be removed. Alternatively, the need may arise to remove the proximal body if the version (or angle) needs to be corrected. In such a case, the surgeon will need to remove the body and adjust the angle of the proximal body relative to the distal stem.

A disassembly tool may also be needed if, after implantation, the implant needs to be removed. One method of removing the implant would be to attach the entire construct to a slap hammer and remove both pieces at once. However, if there has been substantial bone in-growth into the stem, this can be very difficult. Another method would be to disassemble the proximal body from the stem, and then use a trephine to cut out the distal stem. This option preserves more bone and is the most feasible option. Thus, a tool needs to be developed that can disassemble the proximal body from the distal stem while the stem is implanted and fixed in the femur.

SUMMARY

According to one embodiment of the present invention, a disassembly tool for disassembly of a first component of a prosthesis to a second component of the prosthesis for use in joint arthroplasty is provided. The tool includes a first member having a radial portion operably associated with the first component and adapted to exert a radial force on the first component. The tool further includes a second member operably associated with the second component. The second member has a second member longitudinal axis. Also included is a drive mechanism coupled to the second member, such that as the drive mechanism is activated, the second member exerts a force against the second component in the direction of the longitudinal axis. The exertion of force against the second member further causes the second member to move relative to the first member along the second member longitudinal axis.

According to another embodiment of the present invention, a method for disassembling a first component of a prosthesis to a second component of the prosthesis for use in joint arthroplasty is provided. The method includes using a disassembly tool having a first member, a second member having a longitudinal axis and coupled to the first member, and a drive mechanism coupled to the second member. A distal portion of the second member is inserted into a recess of the second component. A proximal portion of the first component abuts the first member. A radial force is exerted on the first component. The drive mechanism is activated, causing the second member to exert a force along the longitudinal axis against the second component.

According to yet another aspect of the present invention, a kit for use in hip arthroplasty is provided. The kit includes a first component of a prosthesis and a second component of a prosthesis. The second component is coupled to the first component. The kit further includes a disassembly tool for disassembling the first component from the second component of the prosthesis for use in joint arthroplasty. The disassembly tool includes a first member having a radial portion operably associated with the first component and adapted to exert a radial force on the first component. A second member operably associated with the second component is also included. The second member has a second member longitudinal axis. A drive mechanism is coupled to the second member, such that as the drive mechanism is activated, the second member exerts a force against the second component in the direction of the longitudinal axis. Such exertion of force against the second member further causes the second member to move relative to the first member along the second member longitudinal axis.

BRIEF DESCRIPTION OF THE DRAWINGS

For a more complete understanding of the present invention and the advantages thereof, reference is now made to the following description taken in connection with the accompanying drawings.

DETAILED DESCRIPTION OF THE DRAWINGS

Embodiments of the present invention and the advantages thereof are best understood by referring to the following descriptions and drawings, wherein like numerals are used for like and corresponding parts of the drawings.

Figure 1:
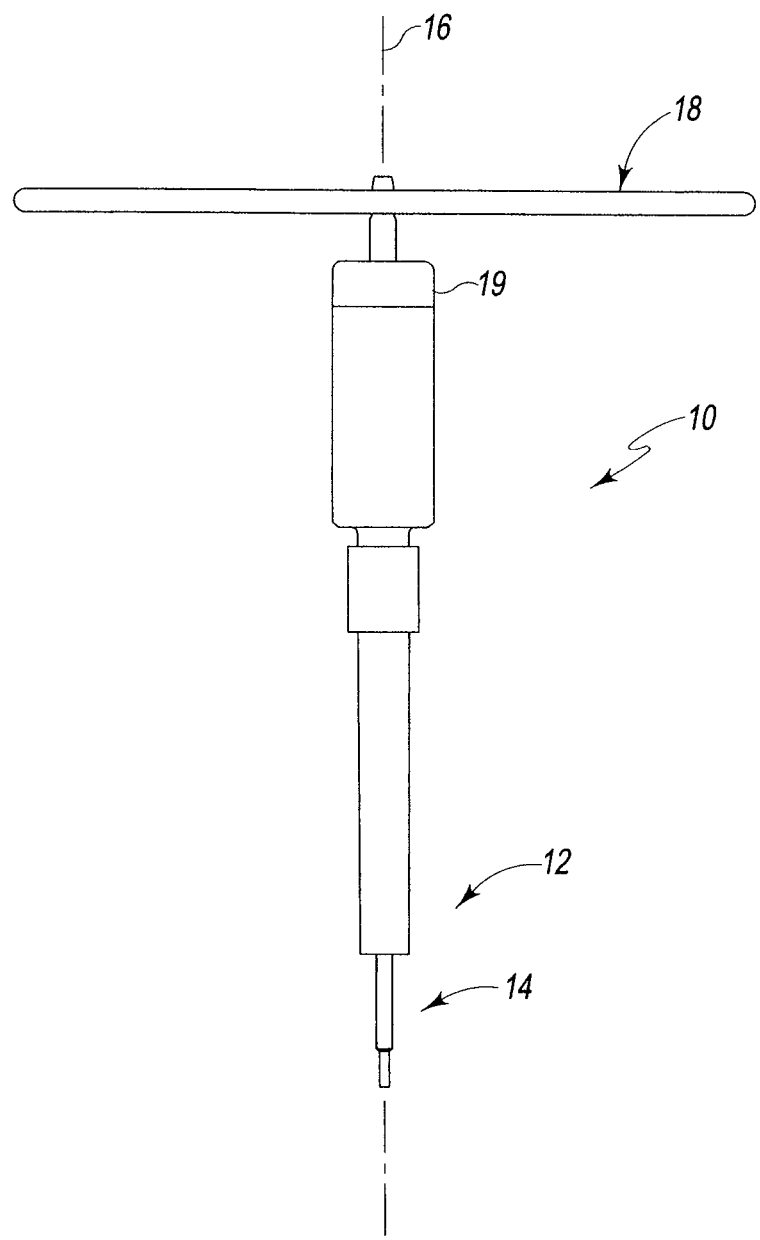
FIG. 1 is a perspective view of a disassembly tool according to one embodiment of the present invention.

FIG. 1 is a perspective view of a disassembly tool 10 according to one embodiment of the present invention. The disassembly tool 10 includes a first member 12 and a second member 14. The second member 14 has a second member longitudinal axis 16. A drive mechanism 18 is coupled to the second member 14. As the drive mechanism 18 is activated, it causes the second member 14 to move relative to the first member 12 along the second member longitudinal axis 16. In the illustrated embodiment, the drive mechanism 18 is a handle that is rotated about the second member longitudinal axis 16. However, in other embodiments, the drive mechanism could be a longitudinal handle, a Hudson connection that connects to a power source, or other known drive mechanism that would cause the second member 14 to move relative to the first member 12 along the second member longitudinal axis 16. In the illustrated embodiment, the first member 12 is coupled to a cap 19 that will be described in more detail below. In some embodiments, there may not be a cap 19.

Figure 2:
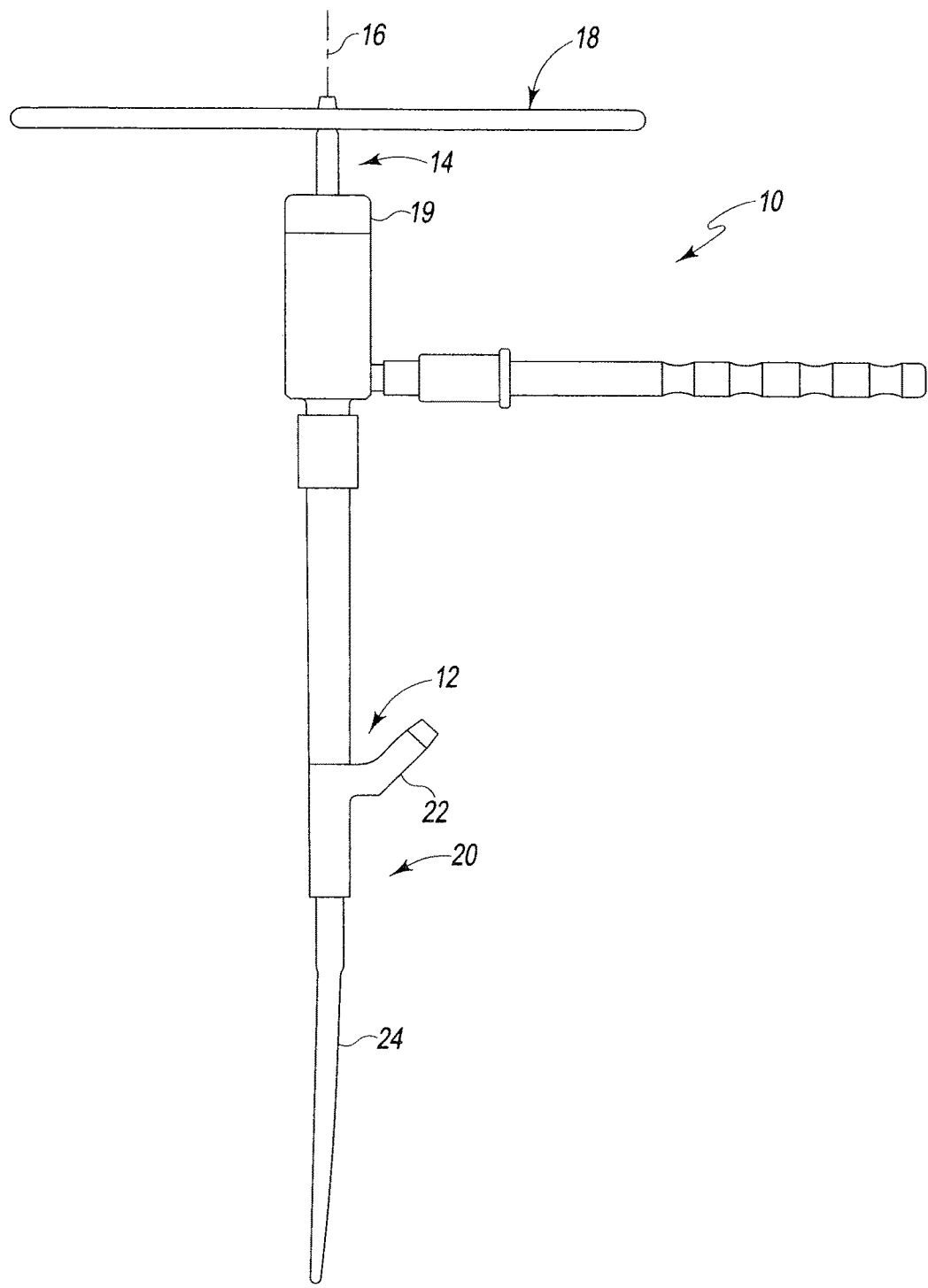
FIG. 2 is a perspective view of the disassembly tool of FIG. 1 coupled with an implant assembly.
Figure 3:
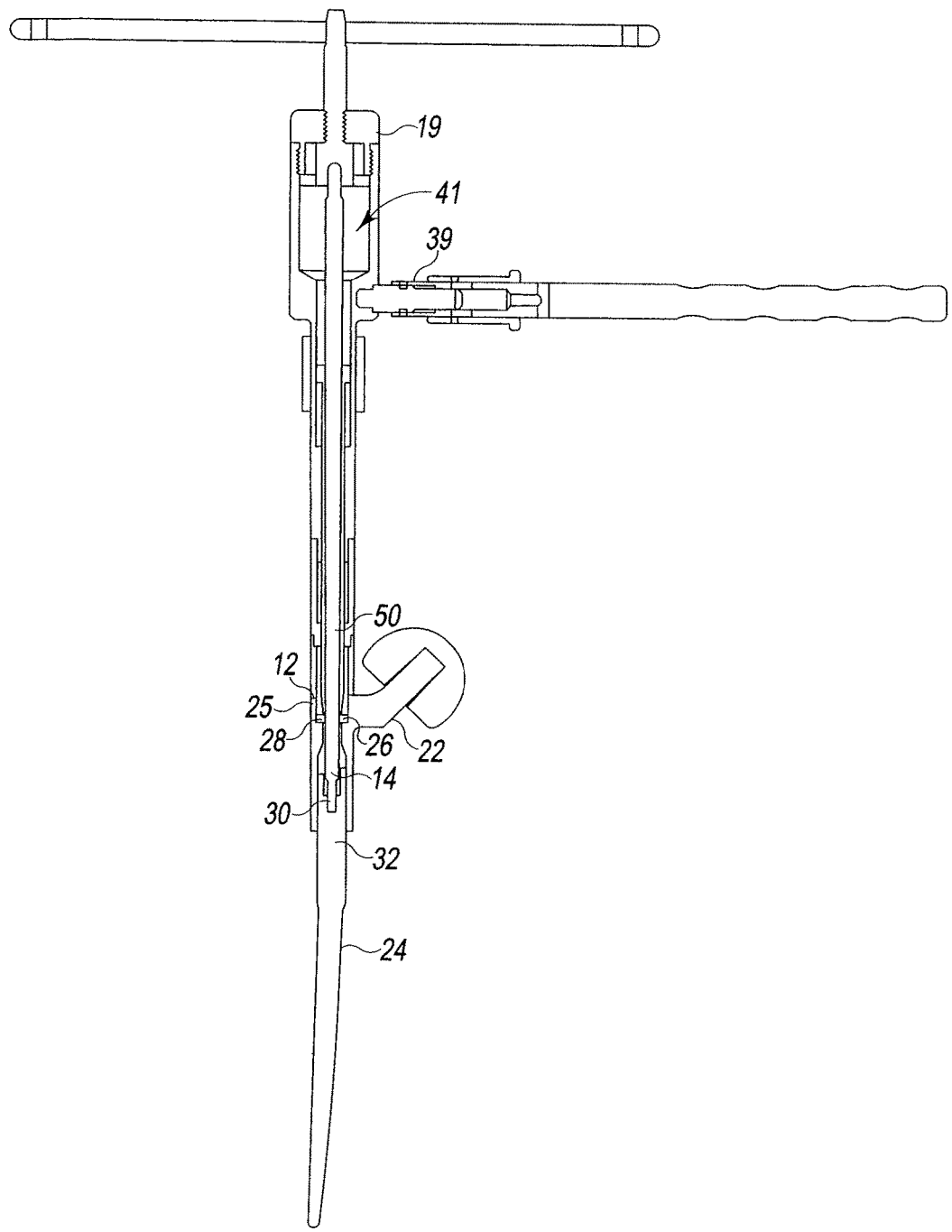
FIG. 3 is a see-through view of FIG. 2.
Figures 4, 5:
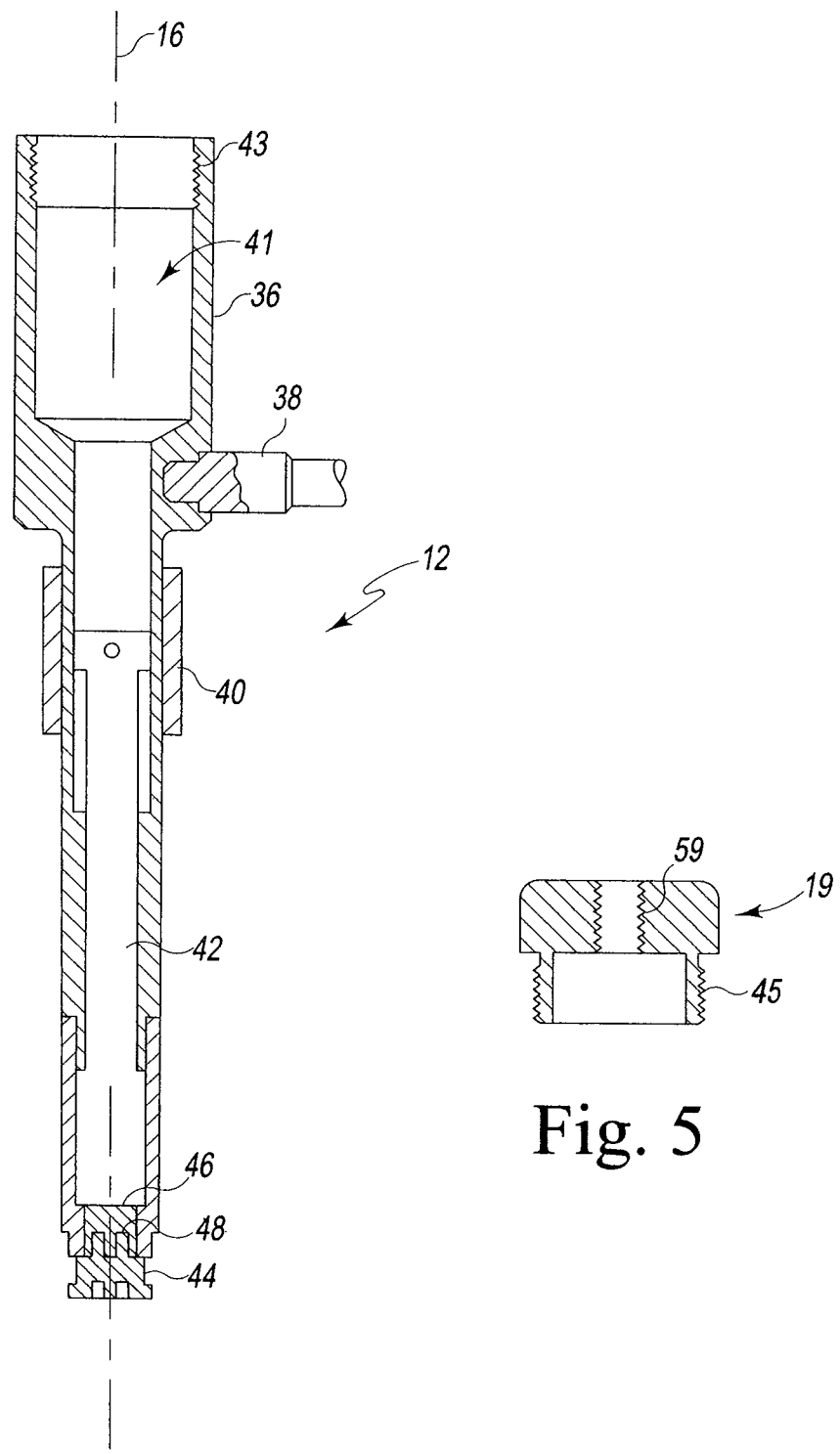
FIG. 4 is a cross-sectional view of a first member according to one embodiment of the present invention.
FIG. 5 is a cross-sectional view of a cap according to one embodiment of the present invention.

Referring now to FIGS. 2 and 3, multiple views of the disassembly tool 10 coupled to a modular implant 20 are shown. As shown, the modular implant 20 includes a first component 22 (or a proximal or neck component) and a second component 24 (or a distal or stem component). The first member 12 of the disassembly tool 10 includes a radial portion 25 at a distal portion 26. The radial portion 25 radially engages a recess 28 of the neck component 22. In the illustrated embodiment, the first member 12 includes a distal portion 26 that is a radially expanding collet 44 (FIG. 4). The radially expanding collet 44 engages the walls defining the recess 28. In other embodiments, other connection means may be used. For example, the distal portion 26 may include threads that engage a threaded recess of the neck component 22. Alternatively, the connection means may be a retractable button/recess system, a slotted l-shaped recess and rod system, or any other known engagement system.

As shown in FIG. 3, a distal portion 30 of the second member 14 engages a proximal portion 32 of the stem component 24. In this embodiment, the distal portion 30 of the second member 14 fits inside a bore of the proximal portion 32 of the stem component 24. In some embodiments, threaded bores and threaded ends may be used. Alternatively, the distal portion 30 of the second member 14 may have the threaded bore and the proximal portion 32 of the stem component 24 may be threaded. In other embodiments, other known means of connecting pieces may be used. For example, an expandable collet may be used. Alternatively, the connection means may be a retractable button/recess system, a slotted l-shaped recess and rod system, an expandable collet system, or any other known engagement system.

Turning now to FIG. 4, a close-up view of the first member 12 will be shown. The first member 12, according to this embodiment, includes a housing 36, a stationary handle 38 coupled to the housing 36, an expansion member 40, an internal sleeve 42 coupled to the expansion member or external collar 40, and an expandable collet 44. The stationary handle 38 may be one piece with the housing 36, or a portion of the housing may connect to the stationary handle 38 via any known connection methods. In one embodiment, a quick-connect connection 39 (FIG. 3) is used, but other embodiments may include threads, tapers, or other known connection methods. The quick-connect feature saves time, since it is an easy way to snap the stationary handle together, although other connections as described above may be used.

The housing 36 includes an internal bore 41 having female threads 43. The female threads 43 will engage corresponding male threads 45 (FIG. 5) of the cap 19. The male threads 45 of the cap 19 slide into the bore 41 and engage the female threads 43 of the bore 41. As shown in FIG. 4, the bore 41 extends all the way through the first member 12 and is designed to receive both the cap 19 and the second member 14 as shown in FIG. 3.

The external collar 40 is coupled to the internal sleeve 42, such that as the external collar 40 is moved along the second member longitudinal axis 16 relative to the housing 36, the internal sleeve 42 also moves along the second member longitudinal axis 16 relative to the housing 36. As the internal sleeve 42 moves distally along the second member longitudinal axis 16, a tapered distal portion 46 of the internal sleeve 42 engages a cylindrical inner wall 48 of the expandable collet 44. As the tapered distal portion 46 moves along the cylindrical wall 48, the increasing diameter of the tapered distal portion 46 causes the collet 44 to expand and grasp the inner wall of the proximal body 22 (as shown in FIG. 4). Similarly, as the external collar 40 is moved upwardly (or proximally) along the second member longitudinal axis 16, the internal sleeve 42 also moves upwards along the second member longitudinal 16, disengaging the cylindrical inner wall 48 of the expandable collet 44, allowing the expandable collet to return to its original size.

Although the above embodiment describes a collet 44 having a cylindrical inner wall 48 and the sleeve 42 having a taper, other embodiments may be used. For example, both the collet 44 and the distal portion 46 of the sleeve 42 may have a taper, so long as the tapers differ enough in diameters so that the insertion of the sleeve 42 causes the collet 44 to expand radially. Alternatively, the distal portion 46 of the sleeve 42 may not be tapered, it may have a cylindrical shape, so long as the diameter is greater than that of the inner wall of the collet 44.

Figure 6:
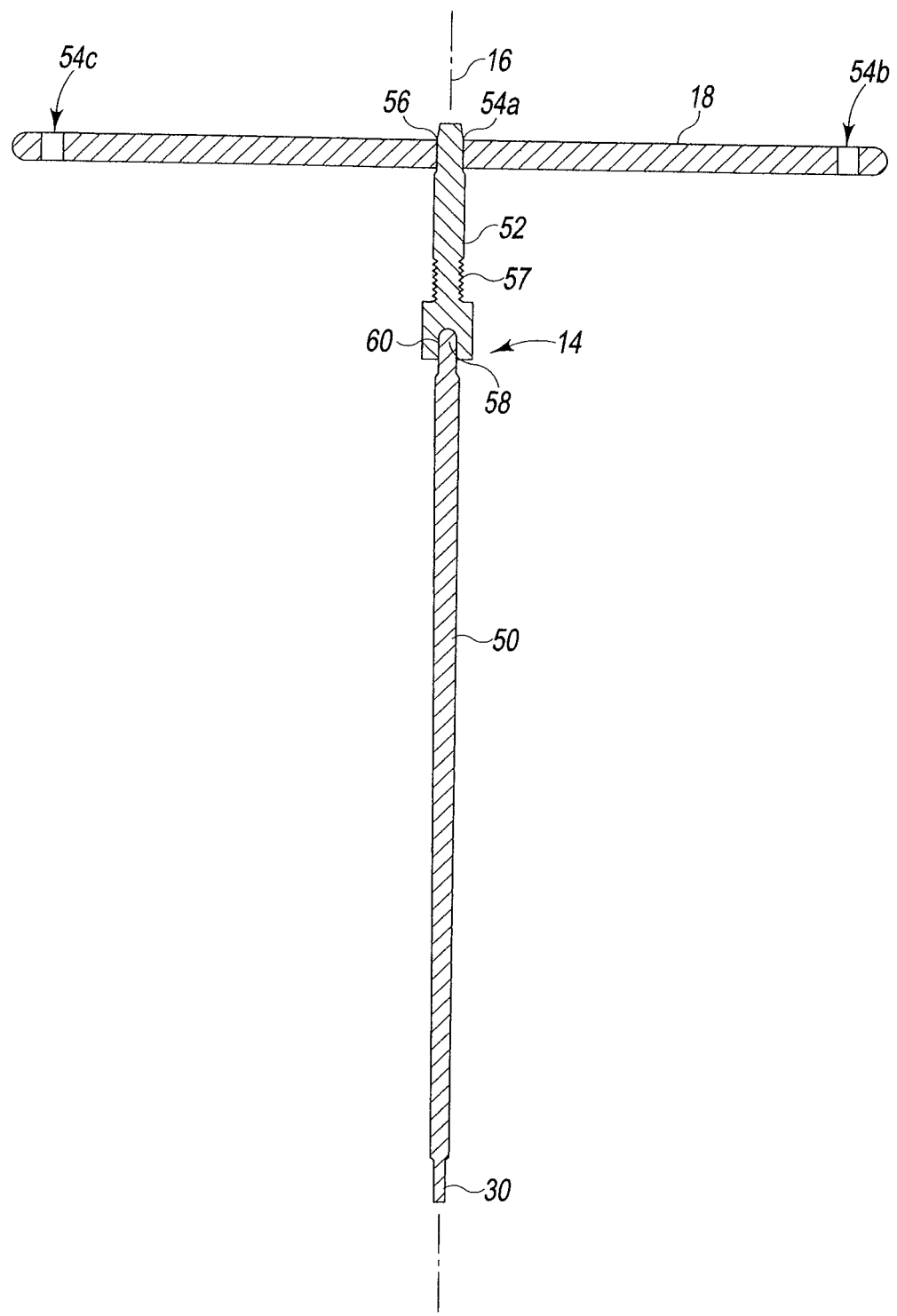
FIG. 6 is a perspective view of a second member according to one embodiment of the present invention.

Turning now to FIG. 6, the second member 14 and drive mechanism 18 will be described in more detail. As shown in FIG. 6, the second member 14 includes, in this embodiment, a push rod 50 and a torque shaft 52. The drive mechanism 18 is coupled to the torque shaft 52. In this embodiment, the drive mechanism 18 includes a central bore 54a, and two outer bores 54b, 54c. A complementary portion 56 of the torque shaft 52 is configured to engage any of the three bores 54a, 54b, 54c, coupling the torque shaft 52 to the drive mechanism 18. In other embodiments, the bore and complementary portion may be switched. Alternatively, other known coupling mechanisms may also be used.

The torque shaft 52 includes male threads 57. The male threads 57 engage female threads 59 on the cap 19 (FIG. 5). The threads 57, 59 connect the torque shaft 52 to the cap 19. The torque shaft 52 is inserted into the central bore 54a of the drive mechanism 18. The drive mechanism 18 is then rotated, causing the torque shaft 52 to rotate. This in turn threads the male threads 57 of the torque shaft 52 into the female threads 59 of the cap 19.

A proximal portion 58 of the push rod 50 is coupled to the torque shaft 52. In the illustrated embodiment, the proximal portion 58 fits within a recess 60 of the torque shaft 52. The proximal portion 58 of the push rod 50 may have an interference fit within the recess 60 of the torque shaft 52. In other embodiments, the proximal portion 58 of the push rod 50 may be coupled to the recess 60 of the torque shaft 52 via a taper lock. Alternatively, the recess may be located on the push rod 50 and the torque shaft 52 may include a protrusion. In other embodiments, other connection mechanisms may be utilized. As shown in FIG. 3, the distal portion 30 of the second member (which coincides with the distal portion of the push rod 50) fits within the recess 28 of the stem 24.

As the drive mechanism 18 is rotated about the second member longitudinal axis 16, the female threads 59 of the cap 19 engages the threads 57 on the torque shaft 52 causing the torque shaft 52 to move downwardly (or distally) along the second member longitudinal axis 16. As the torque shaft 52 moves, the engagement between the torque shaft 52 and the push rod 50 also causes the push rod 50 to move distally (or downwardly) along the second member longitudinal axis 16.

In order to increase the moment when turning the drive mechanism 18, the user can insert the complementary portion 56 of the torque shaft 52 into one of the outer bores 54b, 54c. The user then can utilize the moment of the length of the drive mechanism 18, making the drive mechanism 18 easier to turn. In the illustrated embodiment, the complementary portion 56 is a hex-shaped protrusion and the bores are hex-shaped recesses, such that the two pieces engage one another when the drive mechanism 18 is turned. In other embodiments, different shaped bores and complementary portions may be used. In some embodiments, threaded bores and threaded complementary portions may be used. By utilizing the drive mechanism 18 to do the initial threading and to do the final threading by increasing the moment arm, OR time is reduced. The user only has to pop the drive mechanism 18 on and off. Multiple tools are not needed.

As shown in FIG. 3, the distal portion 30 of the push rod 50 will then abut the bottom of the recess 28 of the stem 24. As the push rod 50 is advanced distally, the stem 24 will also be moved distally. Because the collet 44 is engaging the proximal body 22 and holding the proximal body 22 in position, the engagement between the proximal body 22 and the stem 24 will be broken, allowing the proximal body 22 to be removed separately from the stem 24.

Generally, the disassembly tool 10 may be made from stainless steel. In some embodiments, the various parts of the disassembly tool may be made of different types of stainless steel. In one embodiment, the torque shaft 52 may be made of a hard stainless steel, such as custom 455 stainless steel. The cap 19 may be made of a nitrogen rich stainless steel that is very soft, such as Nitronic 60 stainless steel. The drive mechanism 18 may be made from a stiffer stainless steel. The collet 44 and the push rod 50 may be made from 465 stainless steel. By making the various parts of different materials having different strengths, the wear on the various threaded parts is reduced. Also, the tool 10 may be able to withstand more force without the parts galling or binding. In other embodiments, some of the pieces may be made of other biocompatible materials such as plastics or other metals. In some embodiments, the various parts may be all made from the same material.

Figure 7:
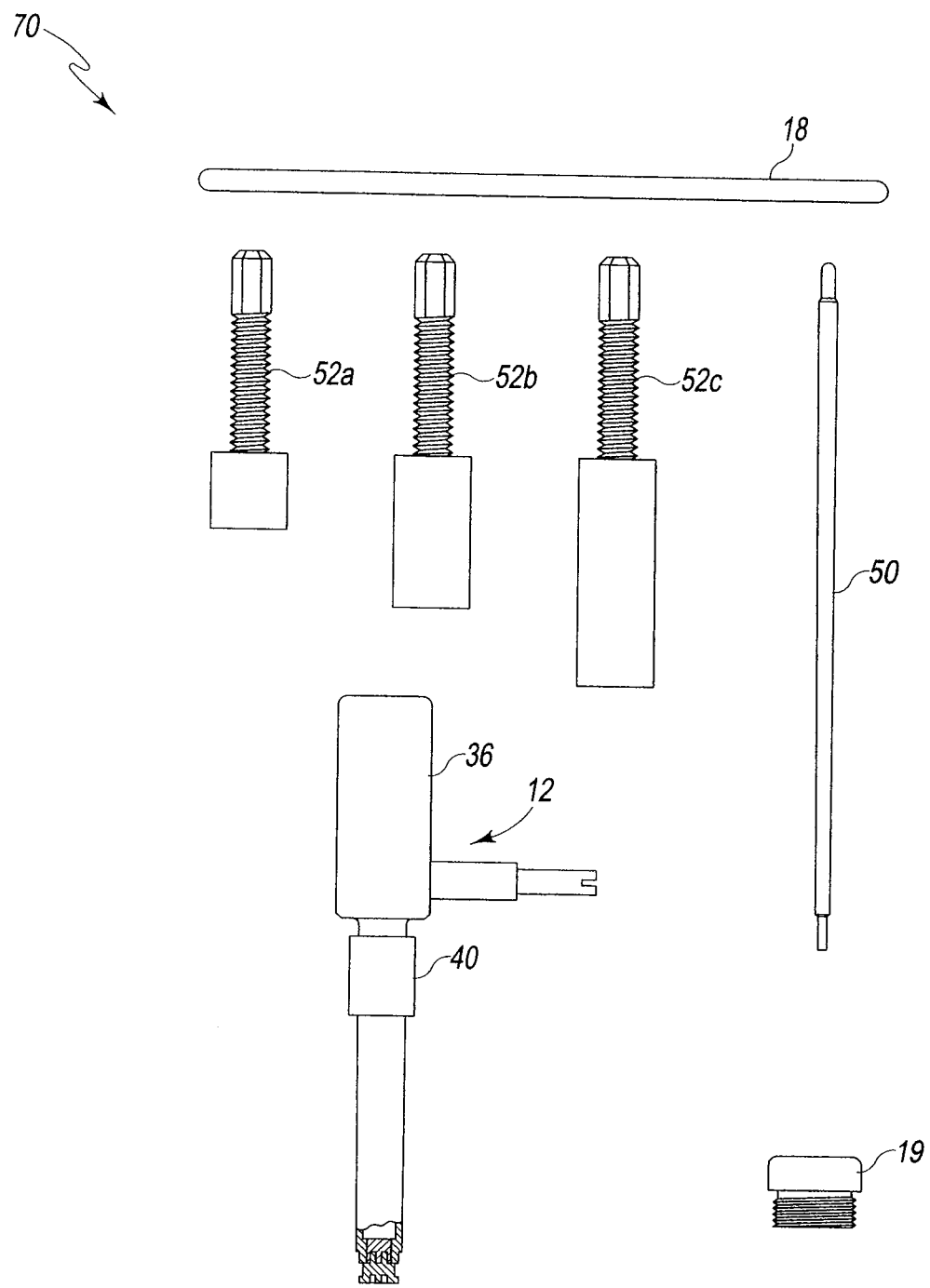
FIG. 7 is a perspective view of a kit according to one embodiment of the present invention.

In some embodiments of the present invention, as shown in FIG. 7, a kit 70 may be provided. In the illustrated embodiment, the kit 70 includes a drive mechanism 18, a plurality of torque shafts 52a, 52b, 52c, a push rod 50, and a first member 12. The plurality of torque shafts 52a, 52b, 52c are of differing lengths. The differing lengths allow the instrument to be used with proximal implants 22 that are of differing lengths. In other words, because the length of the proximal implants 22 varies, the distance between the top of the proximal implant 22 and the stem 24 varies. Although the present kit 70 shows a particular number of torque shafts 52a, 52b, 52c, it should be understood that any number of torque shafts 52a, 52b, 52c may be included in the kit 70. Having multiple torque shafts 52a, 52b, 52c is advantageous because it reduces the time in the OR for the surgeon. The torque shafts 52a, 52b, 52c may be color coded to match a particular proximal body length. The surgeon can then quickly grab the correct torque shaft 52a, 52b, 52c and assemble the tool. If only a single torque shaft 52 were included, it would need to be adjustable to account for the various lengths of different proximal bodies.

Figure 8:
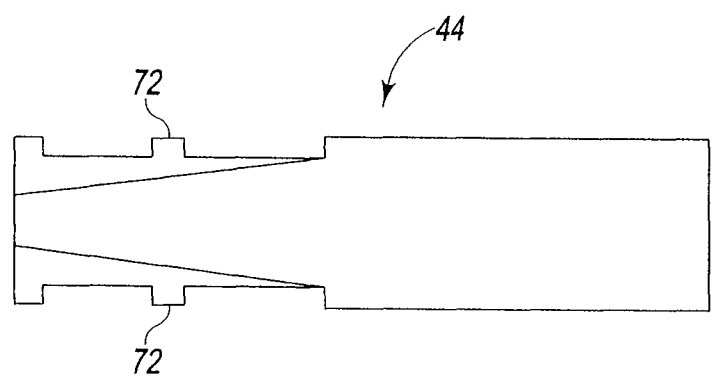
FIG. 8 is a cross-sectional view of an expandable collet according to one embodiment of the present invention.

As shown in FIG. 8, a cross-sectional view of the collet 44 according to one embodiment of the present invention is illustrated. As shown in FIG. 8, the collet 44 includes a plurality of ribs 72 that extend radially from the collet 44. In this embodiment, the ribs 72 reinforce the strength of the collet 44. In other embodiments, the collet 44 may not have the ribs 72.

Figure 9:
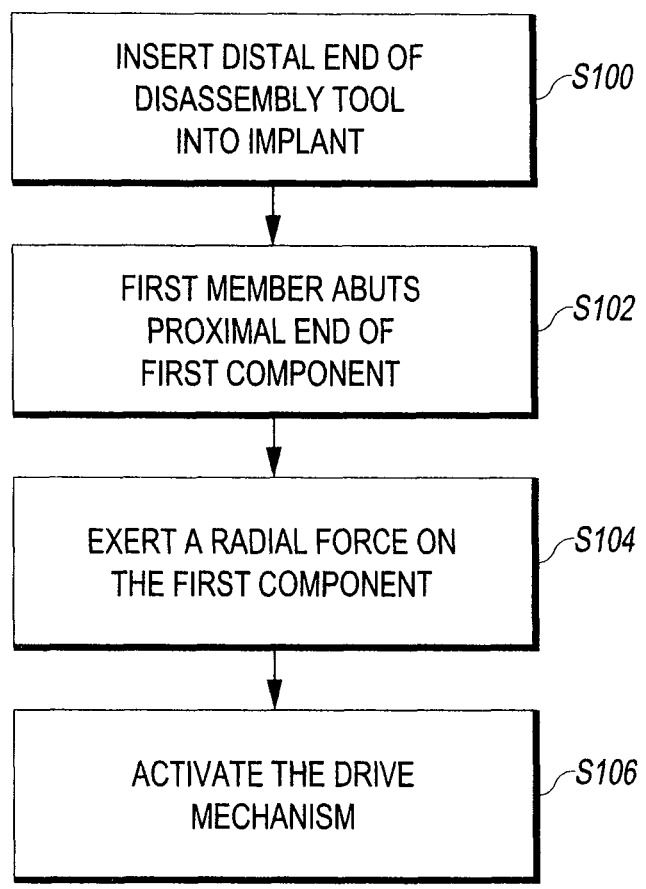
FIG. 9 is a flow chart illustrating the method of using a disassembly tool according to one embodiment of the present invention.

Turning now to FIG. 9, a flow chart describing the method of using the disassembly tool 10 is shown. At step s100, the distal portion of the second member is inserted into the recess of the second component. The first member then abuts the proximal portion of the first component (step s102). A radial force is exerted on the first component at step s104. This may be achieved by activating the radially expanding collet as described above. At step s106, the drive mechanism is activated, causing the second member to exert a force in the longitudinal direction against the second component. Activating the drive member in some embodiments includes rotating a moveable handle about the longitudinal axis, causing the second member to move distally along the longitudinal axis, engaging a bottom wall of the recess in the second component.

Although the present invention and its advantages have been described in detail, it should be understood that various changes, substitutions, and alterations could be made therein without departing from the spirit and scope of the present invention as defined by the appended claims.

We claim:

1. A kit for use in hip arthroplasty, comprising:
a first component of a prosthesis;
a second component of a prosthesis, the second component coupled to the first component; and
a disassembly tool for disassembling the first component from the second component of the prosthesis for use in joint arthroplasty, the disassembly tool including
a first member having a radial portion operably associated with the first component and adapted to exert a radial force on the first component,
a second member operably associated with the second component, the second member having a second member longitudinal axis, and
a drive mechanism coupled to the second member, such that as the drive mechanism is activated, the second member exerts a force against the second component in the direction of the longitudinal axis, wherein such exertion of force against the second member further causes the second member to move relative to the first member along the second member longitudinal axis;
wherein the radial portion is a radially expandable collet and wherein the first member includes an external collar, an internal sleeve coupled to the external collar and the radially expanding collet, wherein as the external collar is moved along the longitudinal axis, the internal sleeve is moved along the internal axis and the radially expanding collet, expands radially into a recess on the first component.

2. The kit of claim 1, wherein the first and second component are coupled to one another via a taper lock.

3. The kit of claim 1, wherein the first component includes a recess in a proximal portion and the radial portion of the first member fits within the recess of the first component.

4. The kit of claim 1, wherein the radially expanding collet includes reinforcing ribs.

5. The kit of claim 1, wherein the radially expanding collet includes a cylindrical recess and the internal sleeves includes a tapered wall that engages the cylindrical recess.

6. The kit of claim 1, wherein the drive mechanism includes a handle, a torque shaft in threaded engagement with the handle, and a push rod coupled to the torque shaft, wherein the push rod engages a recess in the second component.

* * * * *